United States Patent [19]

Mares et al.

[11] Patent Number: 4,625,023

[45] Date of Patent: Nov. 25, 1986

[54] SELECTIVE CONVERSION OF ALIPHATIC AND AROMATIC AMINONITRILES AND/OR DINITRILES INTO LACTAMS

[75] Inventors: Frank Mares, Whippany; Reginald Y. Tang, Warren; James E. Galle, Madison; Rose M. Federici, Princeton, all of N.J.

[73] Assignee: Allied Corporation, Morris Township, Morris County, N.J.

[21] Appl. No.: 771,853

[22] Filed: Sep. 3, 1985

[51] Int. Cl.[4] .................. C07D 201/08; C07D 223/10
[52] U.S. Cl. ..................................... 540/539; 546/243; 546/141; 548/553; 548/472; 548/486; 540/200; 540/451; 540/482; 540/488; 540/492
[58] Field of Search .................. 260/239.3 R, 239.3 B, 260/239 A; 546/243, 141; 548/553, 472, 486

[56] References Cited

U.S. PATENT DOCUMENTS 2,357,484  5/1944  Martin .................. 260/239.3 A

Primary Examiner—Robert T. Bond
Attorney, Agent, or Firm—Richard C. Stewart; Gerhard H. Fuchs

[57] ABSTRACT

Process for the selective conversion of dinitriles into the corresponding lactam by treating the dinitrile with an effective amount of a hydrogenation catalyst such as copper chromite in combination with a co-catalyst, such as titania, at a temperature in the range of from about 200° C. to about 400° C. and at a pressure of at least 50 kPa in the presence of water and hydrogen.

48 Claims, No Drawings

SELECTIVE CONVERSION OF ALIPHATIC AND AROMATIC AMINONITRILES AND/OR DINITRILES INTO LACTAMS

BACKGROUND OF THE INVENTION

1. Field of the Invention

This invention relates to the selective conversion of aliphatic and aromatic dinitriles such as adiponitrile into the corresponding lactam, such as e-caprolactam, by employing a finely divided hydrogenation catalyst, in combination with a finely dispersed co-catalyst. This invention also relates to the selective conversion of a mixture of an aliphatic or aromatic aminonitrile and an aliphatic or aromatic dinitrile into the corresponding lactams by contacting the mixture with a silica catalyst to convert the aminonitrile into the corresponding lactam and thereafter contacting the mixture of lactam and unreacted dinitrile with a hydrogenation catalyst in combination with a cyclization co-catalyst to convert the dinitrile into the corresponding lactam.

2. Prior Art

N-substituted amides, especially 5, 6 and 7 membered lactams, are important raw materials for nylon 4, 5 and 6. Several methods are disclosed in the prior art for preparation of such compounds. For example, U.S. Pat. No. 2,357,484 (E. L. Martin) discloses a vapor phase process for preparing compounds containing the N-substituted amide group, for example, epsilon-caprolactam, by passing a vaporized mixture of water and an aliphatic amino-hydrogen-containing aminonitrile, or a vaporized mixture of water and a nitrile and aminohydrogen-containing amine over a dehydration catalyst such as activated alumina, silica, titanium oxide or borophosphoric acid. U.S. Pat. No. 2,357,484 also discloses that diamides are produced by passing a vaporized mixture of water, dinitriles and monoamines over the dehydration catalyst.

SUMMARY OF THE INVENTION

In one form of this invention, there is provided a process for the selective conversion of aliphatic and aromatic dinitriles into the corresponding lactams which comprises contacting, in the vapor phase, a stream comprising a dinitrile having the formula: $N\equiv C-D-C\equiv N$ wherein D is a divalent organic moiety, with an effective amount of a finely divided hydrogenation catalyst comprising one or more oxides of copper and one or more oxides of chromium in combination with a finely dispersed co-catalyst comprising titania, activated alumina, silica-alumina, zirconia, or mixtures thereof at a temperature in the range of from about 200° C. to about 400° C. and at a pressure of at least about 50 kPa, in the presence of water and hydrogen, and optionally in the presence of ammonia, for a time sufficient to produce the corresponding lactam.

In another form of the present invention, there is provided a process for the selective conversion of a mixture of an aliphatic or aromatic aminonitriles having a formula: $H_2N-D'-C\equiv N$, and an aliphatic or aromatic dinitrile having a formula: $N\equiv C-D-C\equiv N$, wherein D and D' are independently a divalent organic moiety, into the corresponding lactam which comprises:

(a) contacting, in the vapor phase, said mixture with an amount of silica catalyst effective for selectively converting all or a part of said aminonitrile into the corresponding lactam at a temperature in the range of about 200° to about 400° C. and at a pressure of at least about 50 kPa, and in the presence of water and optionally in the presence of hydrogen and ammonia, for a time sufficient to convert all or a portion of said aminonitrile to said lactam; and (b) contacting, in the vapor phase, the unreacted dinitrile, in the presence of said corresponding lactam of said aminonitrile with an amount of a catalytic system effective for selectively converting the dinitrile into the corresponding lactam, said system comprising finely divided hydrogenation catalyst comprising one or more oxides of copper and one or more oxides of chromium with a finely divided co-catalyst comprising titania, activated alumina, silica-alumina, zirconia or mixtures thereof, at a temperature of from about 200° to about 400° C. and at a pressure of at least about 50 kPa and in the presence of water and hydrogen, and optionally in the presence of ammonia, for a time sufficient to convert all or a portion of the dinitrile into the corresponding lactam.

DETAILED DESCRIPTION OF THE INVENTION AND OF THE PREFERRED EMBODIMENTS

The present invention is directed to the preparation of lactams in high yield and high selectivity from aliphatic or aromatic dinitriles, and from mixtures of said aliphatic or aromatic dinitriles and aliphatic or aromatic aminonitriles. In the form of the invention wherein aliphatic or aromatic dinitriles are converted into the corresponding lactam with high selectivity and high yield, a vaporized stream comprising a dinitrile having the formula $N\equiv C-D-C\equiv N$, wherein D is a divalent aliphatic or aromatic moiety, is contacted with an effective amount of a finely dispersed hydrogenation catalyst system comprising one or more oxides of copper and one or more oxides of chromium and a co-catalyst comprising titania, activated alumina, silica/alumina, zirconia or mixtures thereof, at a temperature in the range of from about 200° C. to about 400° C. and at a pressure of at least about 50 kPa in the presence of water and hydrogen and optionally in the presence of ammonia for a time sufficient to produce the corresponding lactam.

The aliphatic or aromatic dinitriles useful in the process of the present invention have the formula $N\equiv C-D-C\equiv N$ wherein D is a divalent organic moiety having the formula:

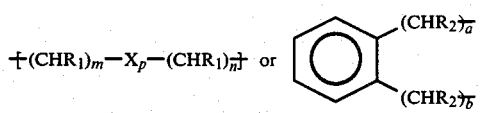

wherein:

X is O or NR';

R' is hydrogen, alkyl or alkenyl having from about 1 to about 8 carbon atoms, or alkoxyalkyl having from about 2 to about 8 carbon atoms;

n and m are integers selected such that n+m is about 2, 3, 4, 5, or 6;

p is about 0 or 1;

$R_1$ is the same or different at each occurrence and is hydrogen or alkyl having from 1 to about 8 carbon atoms;

$R_2$ is the same or different at each occurrence and is hydrogen or alkyl having from 1 to about 4 carbon atoms; and a and b are integers selected so that a+b is 1 or 2.

Illustrative of dinitriles which are useful in the conduct of the process of the present invention are $$N\equiv C-(CH_2)_2-C\equiv N,$$

$$N\equiv C-(CH_2)_3-C\equiv N,$$

$$N\equiv C-(CH_2)_4-C\equiv N,$$

$$N\equiv C-(CH_2)_5-C\equiv N,$$

$$N\equiv C-(CH_2)_6-C\equiv N,$$

$$N\equiv C-(CH_2)_2-O-CH_2-C\equiv N,$$

$$N\equiv C-(CH_2)_2-O-(CH_2)_2-C\equiv N,$$

$$N\equiv C-(CH_2)_2-N-CH_3-(CH_2)_2-C\equiv N,$$

$$\overset{CH_2CH_2CH_3}{\underset{|}{N\equiv C-CH-CH_2-C\equiv N}}$$

$$N\equiv C-(CH_2)_2-C_6H_4-CH_2-C\equiv N,$$

$$N\equiv C-CH_2-CH(CH_3)-C_6H_4-CH_2C\equiv N.$$

Other dinitriles not listed above which are obvious in view of this disclosure are considered within the scope of the present invention so long as the dinitrile and corresponding lactam have vapor pressures sufficient to remain in the gaseous state under the conditions of the present invention. The preferred dinitriles are those in which D is a moiety of the formula:

$$-CH_2)_n$$

wherein:

n is equal about to 2, 3, 4 or 5.

The catalyst compositions found useful in the present invention for the conversion of a dinitrile into the corresponding lactam include a finely divided hydrogenation catalyst system comprising one or more oxides of copper and one or more oxides of chromium, and a finely divided co-catalyst. By the term "finely divided" or "finely dispersed" as used herein in reference to catalyst composition is meant a particle size of no more than about 45 microns, preferably no more than about 30 microns. Illustrative of such useful oxides are mixtures of copper(I) chromite, copper(II) chromite and the like. The catalyst system also includes a finely divided co-catalyst comprising titania, activated alumina, alumina, silica-alumina or zirconia. The preferred co-catalyst is titania. In the preferred embodiments of the invention the catalyst further comprises one or more stabilizers in an amount sufficient to stabilize the catalyst. Such stabilizers and amounts which should be employed are known in the art and will not be described herein in detail. Illustrative of such stabilizers are barium or maganese-containing substances. The preferred stabilizers are barium oxide and manganese oxide. A particularly useful hydrogenation catalyst includes a copper oxide/chromium oxide/barium oxide of the formula:

$$CuO_x/Cr_2O_y/BaO_z$$

wherein x, y and z are independently about 0, ½, 1, 2 or 3. The copper oxide/chromium oxide/barium oxide hydrogenation catalyst commercially available from Harshaw Chemical Co., Catalog Number Cu-1107, can be used.

The hydrogenation catalyst and co-catalyst may be separately ground to a finely divided powder of particle size of no more than about 45 microns and thereinafter physically mixed. In a preferred embodiment of the present invention the copper oxides/chromium oxides optionally containing a stabilizer such as barium oxide is dispersed onto a suitable co-catalyst such as titania by the incipient wetness technique.

The hydrogenation catalyst may be mixed with or dispersed into the co-catalyst in a weight ratio of from about 10:1 to about 1:10, and preferably from about 1:4 to about 4:1. In a preferred embodiment of the present invention the copper oxides/chromium oxides/barium oxide hydrogenation catalyst is physically mixed with a titania co-catalyst in a weight ratio of from about 1:1 to about 4:1.

Reaction temperatures are usually in the range of about 200° to about 400° C. In the preferred embodiments of the invention, reaction temperatures are from about 250° C. to about 350° C.

Contact times are not critical and can vary widely. Contact times of about 1 to about 10 seconds are preferred.

The process is carried out at a pressure of at least about 50 kPa. In the preferred embodiments of the invention, pressures are from about 50 to about 500 kPa, and in the most preferred embodiments is from about 100 to about 250 kPa. Pressure above atmospheric pressure can be achieved by introducing hydrogen into the enclosed system, either alone or in combination with one or more inert gases such as argon and nitrogen.

The reaction is carried out in the presence of water and hydrogen. Hydrogen may be used in undiluted form, or may be used with an inert diluent gas, such as nitrogen or argon. In general, water is present in the reaction mixture in an amount at least equal to the molar amount of the dinitrile, and the amount of hydrogen is at least equal to twice the amount of dinitrile. In the preferred embodiments of the invention, the amount of water used is from about 1 to about 50 times the molar amount of the dinitrile present, and the amount of hydrogen is from about 2 to about 100 times the molar amount of dinitrile.

Optionally, ammonia may be added to the reaction mixture. In general, the amount of ammonia added is at least equal to the molar amount of the dinitrile used. In the preferred embodiments of the invention, the mole ratio of ammonia to dinitrile initially present in the reaction mixture is from about 1 to about 50.

In the other form of the present invention, a mixture of an aliphatic or aromatic aminonitrile, and an aliphatic or aromatic dinitrile are converted into the corresponding lactam(s) in a two step vapor phase reaction. In the first step, a vaporized mixture of aminonitrile having the formula $H_2N-D'-C\equiv N$, and dinitrile having the formula $N\equiv C-D-C\equiv N$ are contacted in the presence of an amount of a silica catalyst effective for selectively converting only said aminonitrile into the corresponding lactam at a temperature in the range of from about 200° to about 400° C. and at a pressure of at least about 50 kPa, in the presence of water vapor and optionally in the presence of ammonia and hydrogen for a time sufficient to convert said aminonitrile into the corresponding lactam. In step 2, the resulting vaporized mixture of unreacted dinitrile and lactam produced in the first step is contacted with a finely dispersed catalyst system comprising a hydrogenation catalyst comprised of one or more oxides of copper and one or more oxides of chromium, and a finely dispersed co-catalyst selected from the group consisting of titania, activated alumina, aluminia, silica-alumina, zirconia and mixtures thereof at a temperature in the range of from about 200° C. to about 400° C. and at a pressure of at least about 50 kPa and in the presence of water vapor and hydrogen, and optionally in the presence of ammonia, for a time sufficient to produce any amount of the lactam of the dinitrile.

The aliphatic or aromatic aminonitriles useful in the process of the present invention have the formula $HR_1N-D'-C\equiv N$ wherein $D'$ is a divalent organic moiety having the formula:

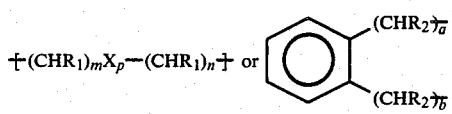

wherein X, R', p, m, n, a, b, $R_1$ and $R_2$ are as defined hereinabove. Illustrative of useful aminonitriles within the scope of the formulae are

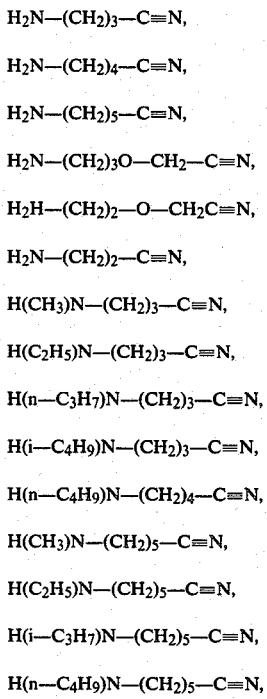

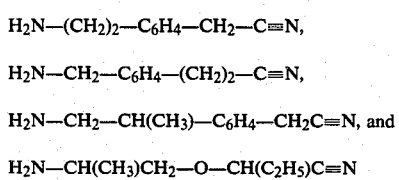

Other aminonitriles obvious in view of this disclosure are considered within the scope of the present invention so long as the aminonitrile and corresponding lactam have vapor pressures sufficient to remain in the gaseous state under the conditions of the present invention. The preferred aminonitriles are those in which D' is of the formula:

wherein:
n is equal to about 2, 3, 4, 5 or 6.

While the aminonitrile and dinitrile in the mixture employed in the first step of the process may be structurally different thereby leading to different lactams, it is preferred to use a mixture of aminonitrile and dinitrile which produce the same lactam. Illustrative of these preferred mixtures are:

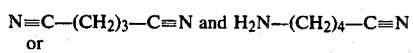
or
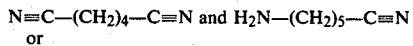
or
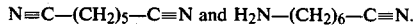

The ratio of aminonitrile to dinitrile may be varied widely. In the preferred embodiments of the invention, the ratio is from about 99:1 to about 1:99 (v/v), and in the most preferred embodiments, is from about 50:50 to about 90:10. A mixture of 30:70 adiponitrile:6-aminocapronitrile is an especially preferred feedstock.

The aliphatic and aromatic dinitriles found useful in the second form of the present invention are exactly those described hereinabove in reference to the first form of the invention.

Among the silica catalysts useful in the process of the first step of the present invention are various acidic, neutral and basic silica catalysts such as granular silica gels which are commercially available from Alfa Ventron, e.g., #89346, The Davison Chemical Division of W. R. Grace, e.g., grades 57, and 59, and especially porous silicas having a substantially spherical shape, as described in more detail below as well as silica obtained by hydrolysis of tetralkylsilicate. However other silicas conveniently having BET surface areas of at least about 100 $m^2/g$ and pore volumes of about 1 $cm^3/g$ may also be used in the process of the present invention. Mixtures of silica with other refractory metal oxides e.g., alumina, titania, magnesia as well as these other refractory metal oxides themselves were found to deleteriously affect the process of the present invention when alkyl or aryl mononitriles or alkylene or arylene dinitriles were present in combination in the aliphatic or aromatic aminonitriles found useful in the present invention and the use of such metal oxide or their mixtures are to be avoided.

The silica catalyts found especially useful in the first reaction step of the process of the present invention are free flowing powders having a substantially spherical shape by transmission electron microscopy, a BET surface area equal to or greater than about 250 $m^2/g$, preferably greater than about 300 $m^2/g$ and more preferably about 300 to about 500 $m^2/g$, a narrow average pore size or pore diameter of equal to or less than about 20 nanometers, preferably in the range of 8 to about 15 nanometers. Such especially useful silicas may be acidic and contain at least about 0.1 wt.% alkali metal or alkaline earth metal oxide. The spherical silica catalysts manufactured by Pechiney-Saint Gobain, France, under the trade name Spherosil and distributed in the United States by Waters Associates, Inc., Milford, MA 01757 under the registered grade XOA400 and PORASIL A are especially useful. The spherical silica grains or beads useful in the present invention may be prepared by calcination at 400°–800° C. of silica gel in the form of small spheres obtained by precipitation of alkali metal silicates or alkylorthosilicates with mineral acids, e.g., $H_2SO_4$ in a liquid immiscible with water (or by crushing the gel in mass) followed by washing, under controlled pH conditions, so that from about 0.1 to about 5 wt. % of alkali metal oxide, e.g., $Na_2O$, remains. See Chemical Abstracts, Vol. 67, 66123G (1967) and British Patent No. 1,171,651, published 11/26/69 (issued to M. Le Page et al. of Pechiney Saint-Gobain) and French Patents Nos. 1,473,239, 1,473,240 and 1,482,867 also to same inventors at Pechiney Saint-Gobain, France.

Temperatures used in the first step of the process are generally in the range of from about 200° C. to about 400° C. Preferred process temperatures are from about 250° C. to about 350° C.

Contact times are not critical and can vary widely. Contact times of from about 1 to about 10 seconds are preferred.

Reaction pressures can be varied widely. The process is carried out at a pressure of at least about 50 kPa. In the preferred embodiments, pressures are from about 50 to 500 kPa, and in the most preferred embodiments, are from about 100 to about 350 kPa. Pressure above atmospheric pressure can be achieved by introducing hydrogen into the system either alone or in combination with an inert gas such as nitrogen or argon.

Both steps of the reaction are carried out in the presence of water. In general, water is present in the reaction mixture in an amount at least equal to the total molar amount of the dinitrile and aminonitrile. In the preferred embodiments of the invention, the amount of water used is from about 1 to about 50 times the total molar amount of the dinitrile and aminonitrile initially present in the reaction mixture. Both steps of the reaction are optionally carried out in the presence of ammonia. In general, the amount of ammonia used is at least equal to the total molar amount of the dinitrile and aminonitrile. In the preferred embodiments, the amounts of ammonia used is from about 1 to about 50 times the total molar amount of the dinitrile and aminonitrile initially present in the reaction mixture.

Step 2 of the reaction is carried out in the presence of hydrogen. In general, the amount of hydrogen employed is at least about two times the total amount of the dinitrile intially present in the reaction mixture. In the preferred emodiments of the invention, the amount of hydrogen used in the second step is from about 2 to about 100 times the total molar amount of dinitrile intially present. In the first step, hydrogen is optional, and if used amounts may vary.

The catalysts, reaction conditions detailed hereinabove as useful in the first form of the present invention wherein dinitriles are converted into lactams are conveniently used for the second step of the second form of the present invention for conversion of dinitrile in the presence of lactam derived from the aminonitrile into lactam.

Both forms of the process of this invention can be conducted in a batch, semicontinuous or continuous fashion. The reaction can be conducted in a single reaction zone or in a plurality of reaction zones, in series or in paralleled or it may be conducted intermittently or continuously in an elongated tubular zone or series of such zones. The materials of construction employed should be inert to the reactants during the reaction and the fabrication of the equipment should be able to withstand the reaction temperatures and pressure.

The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing of the reaction mixture can be employed. Mixing by vibration, shaking, stirring, rotation, oscillation, ultrasonic vibration or the like are all illustrative of the type of agitation means contemplated. Such means are available and well known to those skilled in the art.

The reactants and catalyst may be initially introduced into the reaction zone batchwise or they may be continuously or intermittently introduced in such zone during the course of the process. Means to introduced and/or adjust the quantity of reactants introduced, either intermittently or continuously into the reaction zone during the course of the reaction, can be conveniently utilized in the process especially to maintain the desired molar ratio of the reaction, reactants and catalyst. In the preferred embodiments, the requisite catalyst(s) are charged in the reaction zone, and thereafter the various reactants are introduced in gaseous or vapor form.

Upon completion of the reaction, the reaction mixture is cooled, and the lactam product can be isolated by removing the gaseous ammonia and hydrogen. The desired lactam can then be readily isolated from the aqueous solution by conventional techniques such as crystallization, precipitation, centrifugation and the like.

Lactams prepared in accordance with the process of this invention have many and varied uses. For example, such lactams can be used as precursors in the manufacture of polyamides, as for example, poly(caprolactam). These uses of lactams are well known in the art and will not be described herein in any detail.

The following examples are present to more particularly illustrate the invention and should not be construed as limitations thereon.

GENERAL EXPERIMENTAL CHARACTERIZATION OF PORASIL A AND DAVISON SILICA GEL GRADE 59

A virgin sample of PORASIL A, distributed by Waters Associates, was found to be more acidic than other commerically available silica gels and contain a number of strongly acidic Bronsted acid sites which might be associated with aluminum oxide bonded to silica. See J. N. Armor et al., Journal of Catalysis, Vol. 73, pages 57–65 (1982) at pages 60–63. Virgin samples of PORASIL A and Davison Silica Gel Grade 57 (similar to Grade 59) were analyzed and found to contain the elements listed in Table I of U.S. Pat. application Ser. No. 771,854, filed Sept. 3, 1985.

EXAMPLE 1

A copper/chromium/barium hydrogenation catalyst (obtained from Harshaw Chemical Co. No. 1107T) was tested for the direct formation of caprolactam from 1.90 g of adiponitrile (ADN) at 260° C. in the presence of 6.1 mol% ammonia and 9.3 mol% of water. Under the atmospheric flow heterogeneous catalysis conditions used (hydrogen head pressure was 100 kPa), selectivity to the product caprolactam was 4% at 100% substrate conversion. Major by-products were hexamethylene imine (70%), 2-methylcyclopentanone (12%) and cyclopentanone (2%).

EXAMPLE 2

A powdered copper/chromium/barium (Harshaw 1107T) catalyst of Example 1 was mixed with powdered $TiO_2$ (Harshaw 0720T) at a 50:50 weight ratio. The resulting catalyst was pelletized and a 20–30 mesh sized granules were used for the reaction of adiponitrile (1.90 g) in 6.1 mol% of $NH_3$ and 9.3 mol% of $H_2O$ at 260° C. and a hydrogen head pressure of 100 kPa. The observed selectivities were as follows: 44% to caprolactam, 31% to cyclopentanone, 4% to 2-methylcyclopentanone at 46% substrate conversion. No hexamethylene imine was detected.

EXAMPLE 3

A catalyst obtained by mixing the copper/chromium/barium catalyst of Example 2 with $TiO_2$ at ratio of 80:20 was used. A 66% selectivity to caprolactam was obtained at 41% substrate conversion in the flow reactor operated under conditions of Example 2. By-products were hexamethylene imine (1%) cyclopentanone (7%), and 2-methylcyclopentanone (9%).

EXAMPLE 4

The procedure and reactor of Example 2 was used except that $TiO_2$ (Harshaw 0401P) was used as cocatalyst. The following results were obtained by glc analysis of product effluent: caprolactam (16%S), cyclopentanone (32%S), and 2-methylcyclopentanone (10%S) at 68% substrate (ADN) conversion.

EXAMPLE 5

The results from the atmospheric pressure flow reactor of Examples 1–4 suggested that indeed ADN could be directly converted into caprolactam in a one-step reaction with $H_2/NH_3/H_2O$ over a copper-based catalyst intimately mixed with a cyclization promotion catalyst such as titania. However, the results indicated that these catalysts exhibited very limited life-time (less than 12 hrs.). Higher selectivity and longer catalyst life was then sought through a pressure reaction system and better catalyst preparation.

The catalyst was prepared by thoroughly mixing the powdered Cu/Cr/Ba with the $TiO_2$ catalysts. In the following example, the powdered catalysts were separately grounded and sieved through 45 micron sieves. The sieved catalysts materials were mixed and then filtered through the sieve again. The catalyst powder was then pelletized and sieved to 20–30 mesh. About 5 mL (3.5 g) of the resulting granules were placed on top of a small bed of quartz chips in a stainless steel reactor. A small amount of quartz was placed on top of this catalyst bed. Then 5 g (12 mL) of Porasil A (Waters Associates) were put on top of the quartz chips. For substrate vaporization purposes, a quartz chip bed was placed on top of the Porasil A bed. Reagent gases ($NH_3$, $H_2$) were delivered on top of the quartz bed. The liquid feed was delivered directly into the quartz chip bed. Thermocouples were placed in both the Porasil A and the Cu/Cr/Ba-$TiO_2$ beds.

Thus, the catalysts beds formed a tandem system when the 6-aminocapronitrile (AMN) was first completely converted into e-caprolactam on the Porasil A bed, which left the adiponitrile (ADN) untouched and the ADN was thereafter converted into caprolactam on the Cu/Cr/Ba-$TiO_2$ catalyst. The reactor had built-in sampling capability and a reservoir for the liquid product stream. The pressure was regulated to 137.88 kPa ±6.894 kPa by the $NH_3/H_2$ gas cylinder head pressure regulation. Flow control was obtained by an exit gas valve. Pressure drop across catalyst beds were less than 6.894 kPa initially and during the run. The PORASIL A bed was maintained at 300°–320° C. during the run and the copper/chromium/barium-$TiO_2$ bed was maintained at 268° ±3° C. The gas was a mixture of $NH_3$ (7.3%) in $H_2$. The liquid substrate feed consisted of $NH_4OH/H_2O$/ADN/AMN. Except as indicated this feed was made by mixing 6.6 mL of $NH_4OH$, 23.4 mL of $H_2O$, 15.4 mL of AMN and 6.6 mL of ADN. A diluted feed, when used, consisted of an additional 5.0 mL of water. The catalyst system was reduced by an initial $H_2/N_2$ stream at low $H_2$ ratio and at room temperature. The gas mixture and temperature were then slowly brought to pure $H_2$ and 250° C. within 1 hr. Since the copper/chromium/barium was pre-reduced by the manufacturer, no appreciable exotherm occurred. The results of a continuous run are presented in TABLE I.

TABLE I

SELECTIVE CONVERSION OF AMN/ADN INTO e-CAPROLACTAM

| Sample # | Time (hrs) | $C^2$ % | $S^3$ (%) CL | $S^4$ (%) I |
|---|---|---|---|---|
| 1 | 12 | 100 | 34.4$^a$ | 17.9 |
| 2 | 24 | 100 | 73.7 | 11.0 |
| 3 | 7 | 99.4 | 82.4 | 5.9 |
| 4 | 17 | 97.6 | 85.1 | 4.4 |
| 5 | 26.5 | 91.3 | 85.0 | 2.4 |
| 6 | 22 | 89.9 | 76.3 | 2.3 |
| 7 | 23 | 85.7 | 84.6 | 2.2 |
| 8 | 6.5 | 83.1 | 87.3 | 2.0 |
| 9 | 24 | 85.0 | 91.4 | 1.9 |

FOOTNOTES TO TABLE I
$^a$Mass balance was 58.1% in Sample #1; and in Samples #2–9, the mass balance was in the range of 94.3 to 100%.
[1]Porasil A bed maintained at 300–320° C.; Cu/Cr/Ba—$TiO_2$ bed maintained at 268° ± 3 C.
[2]Conversion (percent) of ADN.
[3]Selectivity (percent) to e-caprolactam (CL).
[4]Selectivity (percent) to hexamethylene imine $(CH_2)_6NH$.

Thus, the best results were obtained when the substrate was diluted (Sample #9): the selectivity to caprolactam was 91% at 85% substrate conversion.

Note that when the copper/chromium/barium-$TiO_2$ catalyst was grounded to less than 100 micron in size, i.e. sieved through 100 micron sieve, a similar reaction gave 74% selectivity to caprolactam, 21% selectivity to hexamethylene imine and 3% selectivity to cyclopentanone at 100% substrate conversion. Using the same catalyst, when only AMN was used instead of the AMN/ADN mixture, selectivity to caprolactam was 93% at 100% substrate conversion.

EXAMPLE 6

Employing the procedure of Example 3 powdered copper chromite (Alfa #11845) and $TiO_2$ (Harshaw 0720T) can be intimately mixed at a weight ratio of 80:20. The intimate mixture can then be used to catalyze the conversion of adiponitrile into caprolactam.

We claim:

1. A process for the selective conversion of a mixture of an aliphatic or aromatic aminonitrile having a formula $H_2N-D'-C\equiv N$ and an aliphatic or aromatic dinitrile having a formula $N\equiv C-D-C\equiv N$ wherein D' and D are independently a divalent organic moiety, into the corresponding lactam which comprises:
   (a) contacting, in the vapor phase, the mixture with an amount of a silica catalyst effective for selectively converting only said aminonitrile into the corresponding lactam at a temperature in the range of from about 200° to about 400° C. and at a pressure of at least about 50 kPa, in the presence of water and optionally in the presence of ammonia, for a time sufficient to convert all or a portion of said aminonitrile into the corresponding lactam; and
   (b) contacting, in the vapor phase, the mixture from step (a) comprising and the unreacted dinitrile and the lactam of said aminonitrile, with a catalyst system comprising a finely dispersed hydrogenation catalyst comprising oxides of copper and chromium in combination with one or more finely dispersed co-catalyst selected from the group consisting of titania, zirconia, alumina, silica/alumina, activated alumina and mixtures thereof at a temperature of from about 200° C. to about 400° C. and at a pressure of at least about 50 kPa in the presence of water and hydrogen, and optionally in the presence of ammonia, for a time sufficient to convert all or a portion of said dinitrile into the corresponding lactam.

2. The process of claim 1 wherein the lactam produced in step (a) is forwarded with the dinitrile to step (b) and wherein the total lactam produced is recovered after step (b).

3. The process of claim 1 wherein in step (a) the silica catalyst has a BET surface area equal to or greater than about 250 m2/g and an average pore diameter equal to or less than about 20 nanometers.

4. The process of claim 3 wherein said catalyst has a BET surface area equal to or greater than about 300 m$^2$/g and an average pore diameter of from about 8 to about 15 nanometers.

5. The process of claim 4 wherein said catalyst has a BET surface area between about 300 m$^2$/g and about 500 m$^2$/g.

6. The process of claim 1 wherein in step (a) the silica catalyst is acidic and contains at least about 0.1 wt. % alkali metal or alkaline earth metal oxide and at least about 0.1 wt. % of a Group IIIa or Group Va metal oxide.

7. The process of claim 1 wherein in step (b) said catalyst system further comprises one or more stabilizers.

8. The process of claim 7 wherein said stabilizers are selected from the group consisting of barium (II) or manganese (II) compounds.

9. The process of claim 8 wherein said stabilizers are selected from the group consisting of barium oxide and manganese oxide.

10. The process of claim 9 wherein the catalyst system comprises $CuO_x/Cr_2O_y/BaO_z$ wherein x, y and z are independently 0, ½, 1, 2 or 3.

11. The process of claim 9 wherein the catalyst system comprises $CuO_x/Cr_2O_y/MnO_z$ wherein x, y, and z are independently 0, ½, 1, 2, or 3.

12. The process of claim 1 wherein the average particle size of each of the individual components of said catalyst system of step (b) is equal to or less than about 100 microns.

13. The process of claim 12 wherein said particle size is equal to or less than about 45 microns.

14. The process of claim 13 wherein said particle size is equal to or less than about 30 microns.

15. The process of claim 1 wherein the weight ratio of hydrogenation catalyst to co-catalyst in said catalyst system of step (b) is from about 10:1 to about 1:10.

16. The process of claim 15 wherein said ratio is from about 4:1 to about 1:4.

17. The process of claim 16 wherein said ratio is from about 1:4 to about 4:1.

18. The process of claim 1 wherein the amount of water employed in step (a) is at least about equal to the molar amount of aminonitrile, and in step (b) is at least about equal to the molar amount of dinitrile.

19. The process of claim 18 wherein the amount of water employed in step (a) is from about 1 to about 50 times the molar amount of aminonitrile, and in step (b) is from about 1 to about 50 times the molar amount of dinitrile.

20. The process of claim 1 wherein ammonia is employed in steps (a) and (b).

21. The process of claim 20 wherein the amount of ammonia employed in step (a) is from about 1 to about 50 times the molar amount of aminonitrile, and in step (b) is respectively from about 1 to about 50 times the molar amount of dinitrile.

22. The process of claim 1 wherein the amount of hydrogen employed in step (b) is at least about two times the molar amount of dinitrile.

23. The process of claim 22 wherein the amount of hydrogen empoloyed is from about 2 to about 100 times the molar amount of dinitrile.

24. The process of claim 1 wherein the divalent organic moieties D and D' are the same or different and are of the formula:

$$-(CHR_1)_m-X_p-(CHR_1)_n- \text{ or }$$

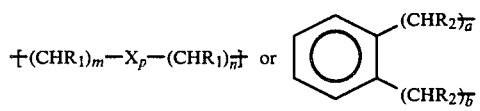

wherein:
X is O or NR';
R' is hydrogen, alkyl or alkenyl having from about 1 to about 8 carbon atoms, or alkoxyalkyl having from about 2 to about 8 carbon atoms;
$R_1$ can be the same or different in each occurence and is hydrogen, alkyl or alkenyl having from 1 to about 8 carbon atoms, or alkoxyalkyl having from 2 to about 8 carbon atoms;
n and m are integers and are selected such that n+m is equal to 2, 3, 4, 5, or 6;
p is 0 or 1;
a and b are integers and are selected such that a+b is 1 or 2; and
$R_2$ is the same at each occurrence and is hydrogen or alkyl having from 1 to about 4 carbon atoms.

25. The process of claim 1 wherein D is of the formula:

$$-(CH_2)_n-$$

wherein:
n is equal to 1, 2, 3, 4 or 5.

26. The process of claim 1 wherein D' is of the formula:

$$-\text{CH}_2)_n$$

wherein:
n is equal to 2, 3, 4, 5 or 6.

27. The process of claim 1 wherein the reaction temperature is from about 250° C. to about 350° C.

28. The process of claim 1 wherein the reaction pressure is from about 50 to about 400 kPa.

29. A process for the selective conversion of aliphatic and aromatic dinitriles into the corresponding lactams which comprises contacting, in the vapor phase, a stream comprising dinitrile having the formula NC—D—CN wherein D is a divalent organic moiety with an effective amount of a catalyst system comprising a finely divided hydrogenation catalyst comprising oxides of copper and of chromium and a finely dispersed co-catalyst comprising at least one of titania, aluminia, activated alumina, alumina/silica, zirconia, or mixtures thereof at a temperature in the range of about 200° to about 400° C. and at a pressure of at least about 50 kPa, in the presence of water and hydrogen, and optionally in the presence of ammonia, for a time sufficient to produce the corresponding lactam of said dinitrile.

30. The process of claim 29 wherein the catalyst further comprises one or more stabilizers.

31. The process of claim 30 wherein said stabilizers are selected from the group consisting of barium (II) or manganese (II) compounds.

32. The process of claim 31 wherein said stabilizers are selected from the group consisting of barium oxide and manganese oxide.

33. The process of claim 32 wherein said catalyst comprises $\text{CuO}_x/\text{Cr}_2\text{O}_y/\text{BaO}_z$, wherein x, y and z are independently 0, ½, 1, 2 or 3.

34. The process of claim 33 wherein said catalyst comprises $\text{CuO}_x/\text{Cr}_2\text{O}_y/\text{MnO}_z$, wherein x, y and z are independently 0, ½, 1, 2 or 3.

35. The process of claim 29 wherein the average particle size of each of the individual components of said catalyst is equal to or less than about 100 microns.

36. The process of claim 35 wherein said size is equal to or less than about 45 microns.

37. The process of claim 36 wherein said size is equal to or less than about 30 microns.

38. The process of claim 24 wherein said cocatalyst is titania.

39. The process of claim 29 wherein the weight ratio of said hydrogenation catalyst to said co-catalyst in said system is from about 10:1 to about 1:10.

40. The process of claim 39 wherein said ratio is from about 4:1 to about 1:4.

41. The process of claim 29 wherein the amount of water is at least about equal to the molar amount of dinitrile.

42. The process of claim 41 wherein the amount of water is from about 1 to about 50 times the molar amount of dinitrile.

43. The process of claim 29 wherein ammonia is employed.

44. The process of claim 29 wherein the respective amount of hydrogen is at least about 2 times the molar amount of dinitrile.

45. The process of claim 44 wherein said respective amount hydrogen is from about 2 to about 100 times the molar amount of dinitrile.

46. The process of claim 29 wherein said reaction temperature is from about 250° C. to about 350° C.

47. The process of claim 29 wherein the reaction pressure is from about 50 to about 500 kPa.

48. The process of claim 29 wherein the divalent organic moieties D and D' are the same or different and are of the formula:

$$-\!\!\left(\text{CHR}_1\right)_m\!-\!\text{X}_p\!-\!\left(\text{CHR}_1\right)_n\!\!- \text{ or }$$

[benzene ring with substituents $(\text{CHR}_2)_a$ and $(\text{CHR}_2)_b$]

wherein:
X is O or NR';
R' is hydrogen, alkyl or alkenyl having from about to about 8 carbon atoms, or alkoxyalkyl having from about 2 to about 8 carbon atoms;
$R_1$ is the same or different at each occurence and is hydrogen, alkyl or alkenyl having from 1 to about 8 carbon atoms, or alkoxyalkyl having from 2 to about 8 carbon atoms;
n and m are integers and are selected such that n+m is equal to 2, 3, 4, 5, or 6;
p is 0 or 1;
a and b are integers and are selected such that a+b is equal to 1 or 2; and
$R_2$ is the same or different at each occurrence and is hydrogen or alkyl having from 1 to about 4 carbon atoms.

* * * * *